(12) United States Patent
Zhou

(10) Patent No.: US 9,089,425 B2
(45) Date of Patent: Jul. 28, 2015

(54) ACTIVE HYDRAULIC VENTRICULAR ATTACHING SUPPORT SYSTEM

(75) Inventor: Xiaohui Zhou, Nanjing (CN)

(73) Assignees: Xiaohui Zhou, Nanjing, Jiangsu (CN); Lei Han, Nanjing, Jiangsu (CN); Li Zhou, Nanjing, Jiangsu (CN); Yuyan Zhou, Nanjing, Jiangsu (CN)

( * ) Notice: Subject to any disclaimer, the term of this patent is extended or adjusted under 35 U.S.C. 154(b) by 716 days.

(21) Appl. No.: 13/319,520

(22) PCT Filed: Apr. 30, 2010

(86) PCT No.: PCT/CN2010/000611
§ 371 (c)(1),
(2), (4) Date: Nov. 8, 2011

(87) PCT Pub. No.: WO2010/127553
PCT Pub. Date: Nov. 11, 2010

(65) Prior Publication Data
US 2012/0059214 A1 Mar. 8, 2012

(30) Foreign Application Priority Data

May 8, 2009 (CN) .......................... 2009 1 0031330

(51) Int. Cl.
*A61F 2/24* (2006.01)
*A61M 1/10* (2006.01)

(52) U.S. Cl.
CPC ............ *A61F 2/2481* (2013.01); *A61M 1/1068* (2013.01); *A61M 1/106* (2013.01)

(58) Field of Classification Search
CPC ............................. A61M 1/106; A61F 2/2481
USPC .............. 600/16, 37; 604/890.1, 305; 602/48; 428/221
See application file for complete search history.

(56) References Cited

U.S. PATENT DOCUMENTS

| | | | | |
|---|---|---|---|---|
| 4,705,508 A | * | 11/1987 | Karnavas et al. | 604/113 |
| 5,150,706 A | * | 9/1992 | Cox et al. | 607/105 |
| 6,626,821 B1 | * | 9/2003 | Kung et al. | 600/16 |
| 7,252,632 B2 | * | 8/2007 | Shapland et al. | 600/37 |
| 7,468,029 B1 | * | 12/2008 | Robertson, Jr. | 600/37 |
| 2004/0010180 A1 | * | 1/2004 | Scorvo | 600/16 |
| 2004/0059181 A1 | * | 3/2004 | Alferness | 600/16 |
| 2010/0269881 A1 | * | 10/2010 | Scheller | 136/242 |

* cited by examiner

*Primary Examiner* — Mark W Bockelman

(57) ABSTRACT

An active hydraulic ventricular attachable support system includes a net cover for surrounding a ventricle and is formed by hollow tubes. All the hollow tubes can completely communicate with each other or form a plurality of independent areas, and the interior of each independent area is intercommunicating, while the independent areas are not communicating with each other. The system as a whole is positioned on the surface of the heart. The hollow tubular structure can be filled with various kinds of liquid of different physical characteristics, and then the corresponding reaction pressure generated can be applied to the ventricle and the surfaces of the heart. The system also can be incorporated with local administration.

14 Claims, 4 Drawing Sheets

ACTIVE HYDRAULIC VENTRICULAR ATTACHING SUPPORT SYSTEM

BACKGROUND OF THE PRESENT INVENTION

1. Field of Invention

The present invention relates to a device for treating various kinds of heart diseases, and more particularly to an active hydraulic ventricular attaching support system for treating heart failure or various kinds of cardiomyopathies.

2. Description of Related Arts

Heart failure is a common pathologic and physiologic state of most heart diseases which have developed to the end stage, and is also a clinical syndrome of ventricular filling or impaired ejection ability which is caused by the chaos of heart structure and function. Its basic characters are dyspnea and fatigue, limited sporting toleration, and can also be body fluid overload or even pulmonary congestion and surrounding dropsy.

The basic and clinical researches about cardiomyopathies, especially preventing, diagnosing and treating of heart failure have achieved some progress in recent years. However, about 50% of the patients of heart failure die in three years. The heart transplantation is an effective way to treat the end-staged heart failure, but can not be applied widely due to the lacking of donator, and restriction of social, economic and technical factors. Many substituting methods are raised up with respect to the problem.

Cardiac support device (CSD), is a treating harness developed by Acorn Cardiovascular, inc. in 1998, based on the treating concept of passive ventricular constraint (PVC). And its relative patents are: Cardiac harness, U.S. Pat. Nos. 7,485,089, 7,097,613, 7,022,063; Expandable cardiac harness for treating congestive heart failure, U.S. Pat. Nos. 7,097,611,7,081,086, 7,077,802; Cardiac harness for treating congestive heart failure and for defibrillating and/or pacing/sensing, U.S. Pat. No. 7,164,952. The CSD attaches to the epicardium surface tightly and evenly. The methods of transplanting the CSD are disclosed by the following references:

(1) An example of treating expansionary cardiomyopathy with CSD, Chinese Journal of General Surgery, 2004, 42(24): 1508;

(2) Clinical observation to effect of CSD in treating expansionary cardiomyopathy, Chinese Journal of Medicine, 2003, 2(8):51-52;

(3) Application of CSD in treating congestive heart failure, Foreign medicine: angiocardiopathy fascicule, 2004, 31(3): 139-141;

(4) Reverse remodeling of the failing ventricle: surgical intervention with the Acorn Cardiac Support Device, Congest heart Fail, 2004 March-April, 10(2):96-104, discussion 105;

(5) Global surgical experience with the Acorn cardiac support device. J Thorac Cardiovasc Surg, 2003 October, 126(4): 983-91.

The conventional clinical experiments show that, transplanting the CSD for long term helps the left atrium to recover to a normal state, and further makes the shape of heart recover to a normal state. Therefore, CSD is considered as means of good application prospect in treating heart failure.

However, the CSD takes effect by passively physical shaping, and thus has great passivity in application. It can not perform active and positive clinical intervention, especially direct medicine intervention, and can not be combined with modern medicine treatment of various species and good effect. Therefore, its clinical treating effect and treating meaning is discounted and needs to be improved. In general, two main drawbacks should be improved as follows:

(1) passivity of treatment: its treating effect is obtained by passive constriction function without other controlling mechanism, and it can not be intervened in procedure effectively after being transplanted into the body; and (2) uniqueness of treatment: it functions only by physical constriction feature of the fiber net, and can not be combined with other effective treating means such as medicine treatment and synthetical treatment.

SUMMARY OF THE PRESENT INVENTION

1. Technical Problem to be Solved by the Present Invention

With respect to the passivity and uniqueness of the conventional CSD technology, the present invention provides an active hydraulic ventricular attaching support system, which produces direct support effect to various heart diseases by mounting on an outer wall of ventricle. The present invention further provides active physical treating effect capable of controlling the pressure and rhythm. The active hydraulic ventricular attaching support system is connected with an administration system to further provide medicine treating effect.

2. Technical Proposal

Accordingly, in order to accomplish the above objects, the present invention provides an active hydraulic ventricular attaching support system, comprising:

a net cover for surrounding a ventricle, formed by hollow tubes, wherein all the hollow tubes are communicated with each other or form several independent areas, wherein the hollow tubes are communicated with each other within the areas while the areas are not communicated with each other.

The net cover structure formed by the tubes structure is mounted on a heart as an entirety. The hollow tubes structure can be filled various fluids of different physical characters. The fluids produce corresponding reactive pressure with respect to the heart action, effecting on the ventricle. The pressure produced by the passive expansion of the tubular net cover is applied on the heart through constriction of the heart.

A method of transplanting the tube-net structure is similar to the transplantation of the CSD, as recited in the references (1)-(5) in the background. The basic steps thereof comprises: sleeving the tube-net structure structure onto the ventricle, interruptedly suturing an upper edge thereof with atrioventricular groove, and then suturing the tube-net structure in front of the heart in linear according to fitness of the tube-net structure, which should not be too tight, so as to avoid acute restrictive heart dysfunction, wherein decreasing of LVEDD (left ventricular end-diastolic dimension) caused by suturing should be within 10%.

A plurality of apertures are provided on a surface of the hollow tubes forming the net cover, wherein the surface attaches to the ventricular wall. Without the apertures, the system can only provide active hydraulic ventricular attaching and supporting function. But with the apertures, the system can provide not only active hydraulic ventricular attaching and supporting function, but also administrating function. Accordingly, the medicine compound or embryonic stem cell or bone marrow stem cell in the fluid inside the tubes can effect on cardiac muscle directly, and produce direct pharmacological action under high local concentration on cardiac muscle or other heart tissues without entering blood circulation.

No matter with or without the apertures, the net cover has two or more ends connected to an exterior of body, and each of the independent areas forming the net cover has two or more ends connected to the exterior of body. The ends connected to the exterior of body are connected with a main body of the net cover by seamless and integrated tubules which are communicated with the tubes system of the main body of the net cover integratedly and can be filled with various fluids. Additionally, the tubules may have same or different material with the main body of the net cover, and same or different diameter with the main body of the net cover. The ends connected to the exterior of body can be round, elliptic, square, or other shapes, which are only limited to connecting with instruments or equipments outside the body with good sealing and firmly connection, so as to avoid any gap or hole, any leaking of gas or fluid inside the tubes, or entering of external fluid, gas, solid or microorganism into the tubes. For realizing basic hydraulic function, each independent area has at least two ends connected with the exterior of body and forming a through way. Therefore, a pressure determined outside the body can be transferred to the ventricle via the fluid inside the tubes, and applies stronger and adjustable restriction effect. Through connecting to the exterior of body, the ends can be further connected with a force pump, which can adjust the pressure of the fluid better.

The net cover with the apertures, can be connected with an administrating system outside the body via the ends connected with the exterior of body. Therefore, medicine from outside can fill and spread all over the net cover, and then apply on the ventricle via the apertures. Accordingly, the species, concentration, and dose of medicine, and speed of administration can be adjusted outside the body, which applies to the heart tissues quickly via the device provided by the present invention.

A membrane can be attached outside the apertures, having selective permeability that selectively allows medicine molecules of certain size, weight, electric quantity, or molecular configuration, so as to further control the species, dose and speed of administration.

When the diameter of the apertures is not larger than a half of the diameter of the hollow tube, the hollow tube performs best. And if the diameter of the apertures is too large, the effect of the hollow tubes will be reduced. Particularly, the diameter of the hollow tubes is 1-2 mm, wherein the diameter of the apertures is 0.5-1.0 mm.

The hollow tubes are made by a flexible material selected from the group consisting of rubber, silica gel, silicone, and other materials of macromolecule and flexible physical character, and especially, selected from nanophase materials capable of loading a medicine.

When the net cover is divided into the several areas, the hollow tubes dividing the areas can have an equal or larger diameter than the rest hollow tubes, i.e., 0.5-2 mm.

A wall of the tubes can be made by nanophase materials capable of loading a medicine, and thus are capable of releasing the medicine.

The net cover is made by gridding formed by tubes in appearance. Before sleeving the ventricle, the density of the gridding is 50-100 per square centimetre on surface, which can also be adjusted according to production process and clinical requirement. It is worth mentioning that, once the net cover is transplanted onto the surface of the heart, the net cover will expands for a certain degree. Therefore, the density of the gridding will change, generally, to be less than that just produced.

3. Beneficial Effect

The present invention provides an active hydraulic ventricular attaching support system which has not only treatment effect of the CSD but also active controllable hydraulic support effect, and further composition effect by combined with local administration. The above effects produce active, positive, and synthetical treatment and restriction effect to stable myocardial ischemia, unstable myocardial ischemia, myocardial infarction, primary organic arrhythmia, expansionary heart diseases, and especially expansionary ventricle of patients of end-staged heart failure, and can be used to treat the above diseases.

The paticular effects are as follows.

(1) Due to the evenness of fluid pressure in the basic structure of the present invention, the device provides more even, lasting, relaxative and stable restriction to the ventricle.

(2) The hollow tubes forming the net cover have the apertures on the wall thereof attaching to the ventricle. Various kinds of fluids are filled inside the tubes. The fluids comprise various medical components, or embryonic stem cells or bone marrow stem cells. Duo to the existing of the apertures, the medicine can directly apply on the cardiac muscle or other heart tissues without entering blood circulation. Therefore, even some medicines which are quite toxic to other organs or tissues of the body but are good to the heart diseases, can also be used without worrying about the toxicity to other organs or tissues. Because the medicines take effect through applying to the heart directly without entering blood circulation, the toxicity to other organs or tissues will not be produced. Accordingly, based on the same reason, the medicine concentration inside the tubes can be very high without worrying about the untoward effect to other organs or tissues. Therefore, under high local concentration, the medicine can produce large direct pharmacological action to the heart, which is obviously better than systemic administration.

(3) No matter with or without the apertures, the net cover has two or more ends connected to an exterior of body, and each of the independent areas forming the net cover has two or more ends connected to the exterior of body. Therefore, a pressure determined outside the body can be transferred to the ventricle via the fluid inside the tubes, and applies stronger and adjustable restriction effect to the ventricle. Through connecting to the exterior of body, the ends can be further connected with a force pump, which can adjust the pressure of the fluid better.

(4) The net cover with the apertures, can be connected with an administrating system outside the body via the ends connected with the exterior of body. Therefore, medicine from outside can spread all over the net cover or concentrate on an independent area of the net cover via the hollow tubes, and then apply on the ventricle via the apertures. Accordingly, the species, dose, and concentration of medicine, time and period of administration, and even the whole administration proposal can be adjusted optionally at any time, so as to have controlling in treatment and further increase the treatment effect.

(5) A membrane can be attached outside the apertures, having selective permeability that selectively allows medicine molecules of certain size, weight, electric quantity, or molecular configuration in a certain speed or flow rate, so as to control the species, size, structure, permeation speed and permeation flow rate of the medicine molecules applying on the heart, and further control the species, dose and spreading speed of the medicine in the heart tissue, and still further help the safety, controlling, effect and economy of clinical administration.

(6) When the diameter of the apertures is not larger than a half of the diameter of the hollow tube, the hollow tube performs best. And if the diameter of the apertures is too large, the effect of the hollow tubes will be reduced. Particularly, the diameter of the hollow tubes is 1-2 mm, wherein the diameter of the apertures is 0.5-1.0 mm. Tubes of diameter within this scope have good support effect to the heart wall, good hydraulic reactivity, and good permeation efficiency to the heart tissue for the medicine.

(7) The hollow tubes are made by a flexible material, so as to make sure that the tubes filled with the fluids have good capacity and flexibility, so as to ensure good hydraulic reactivity for the expected hydraulic ventricle support effect.

(8) The tube wall can adopt nanophase materials capable of loading a medicine. Only if the tube wall materials combine with medicine, the net cover will produce medical treatment effect, so as to combine with the heart wall support effect.

DETAILED DESCRIPTION OF THE PREFERRED EMBODIMENT

Figure 1:
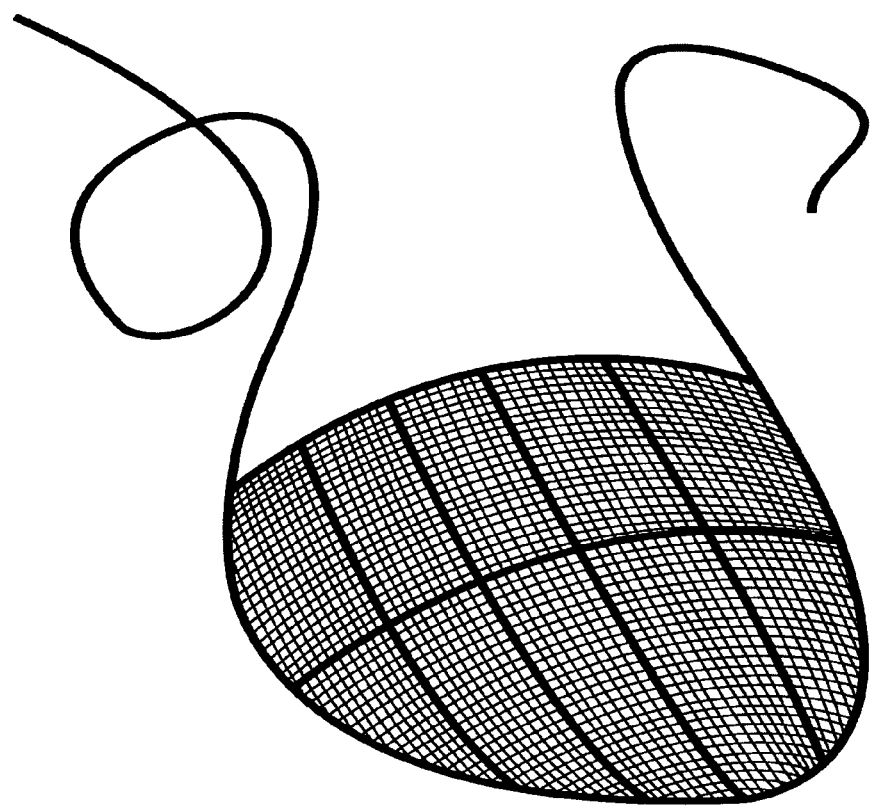
FIG. 1 is a sketch view of a whole structure according to a preferred embodiment of the present invention, illustrating ends connected to an exterior of body.
Figure 2:
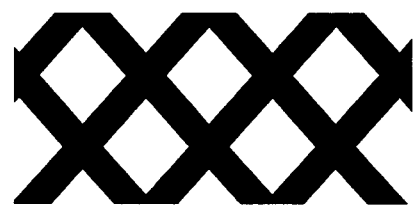
FIG. 2 is a planform view of a side attaching to a ventricle of a net cover without apertures.
Figure 3:
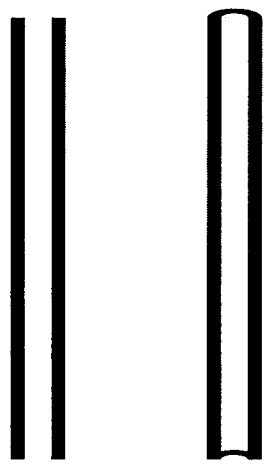
FIG. 3 is a sectional view of tubes of the net cover without apertures.
Figure 4:
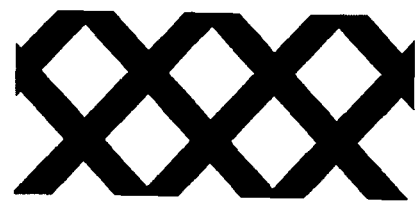
FIG. 4 is a planform view of a side apart from the ventricle of the net cover without apertures.
Figure 5:
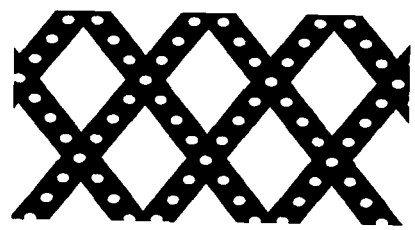
FIG. 5 is a planform view of a side attaching to the ventricle of a net cover with apertures.
Figure 6:
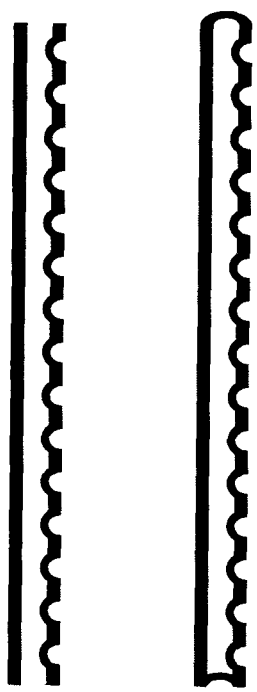
FIG. 6 is a sectional view of tubes of the net cover with apertures.

The present invention is further illustrated with the following examples.

Example 1

An active hydraulic ventricular attaching support system, comprises a net cover surrounding on a ventricle, wherein the net cover is formed by hollow tubes which are made by flexible silicone and have a diameter of 1 mm. All the hollow tubes are communicated completely. The net cover structure formed by the tubes structure is mounted on a surface of the heart as a whole. The hollow tubes are filled with normal saline. The fluid produces corresponding reactive pressure to the ventricle due to heart action. Therefore, restriction effect to the ventricle is lasting, relaxative and stable.

Example 2

An active hydraulic ventricular attaching support system, comprises a net cover surrounding on a ventricle, wherein the net cover is formed by hollow tubes which are made by natural rubber and have a diameter of 1 mm. The rest is the same to the example 1.

Example 3

An active hydraulic ventricular attaching support system, comprises a net cover surrounding on a ventricle, wherein the net cover is formed by hollow tubes which are made by emulsion polymerized butadiene styrene rubber and have a diameter of 1 mm. The rest is the same to the example 1.

Example 4

An active hydraulic ventricular attaching support system, comprises a net cover surrounding on a ventricle, wherein the net cover is formed by hollow tubes which are made by solution polymerized butadiene styrene rubber and have a diameter of 1 mm. The rest is the same to the example 1.

Example 5

An active hydraulic ventricular attaching support system, comprises a net cover surrounding on a ventricle, wherein the net cover is formed by hollow tubes which are made by elastoplastics and have a diameter of 1 mm. All the hollow tubes are communicated completely. The rest is the same to the example 1.

Example 6

An active hydraulic ventricular attaching support system, comprises a net cover surrounding on a ventricle, wherein the net cover is formed by hollow tubes which are made by cis-1,4-polybutadiene rubber and have a diameter of 1 mm. The rest is the same to the example 1.

Example 7

An active hydraulic ventricular attaching support system, comprises a net cover surrounding on a ventricle, wherein the net cover is formed by hollow tubes which are made by polyisoprene rubber and have a diameter of 1 mm. The rest is the same to the example 1.

Example 8

An active hydraulic ventricular attaching support system, comprises a net cover surrounding on a ventricle, wherein the net cover is formed by hollow tubes which are made by neoprene and have a diameter of 1 mm. The rest is the same to the example 1.

Example 9

An active hydraulic ventricular attaching support system, comprises a net cover surrounding on a ventricle, wherein the net cover is formed by hollow tubes which are made by fluoric silica gel and have a diameter of 1 mm. The rest is the same to the example 1.

Example 10

An active hydraulic ventricular attaching support system, comprises a net cover surrounding on a ventricle, wherein the net cover is formed by hollow tubes which are made by hydrogenation butyronitrile gel and have a diameter of 1 mm. The rest is the same to the example 1.

Example 11

An active hydraulic ventricular attaching support system, comprises a net cover surrounding on a ventricle, wherein the net cover is formed by hollow tubes which are made by fluoric rubber and have a diameter of 1 mm. The rest is the same to the example 1.

Example 12

An active hydraulic ventricular attaching support system, comprises a net cover surrounding on a ventricle, wherein the net cover is formed by hollow tubes which are made by silicone rubber and have a diameter of 1 mm. The rest is the same to the example 1.

Example 13

An active hydraulic ventricular attaching support system, comprises a net cover surrounding on a ventricle, wherein the net cover is formed by hollow tubes which are made by chlorine ester rubber and have a diameter of 1 mm. The rest is the same to the example 1.

Example 14

An active hydraulic ventricular attaching support system, comprises a net cover surrounding on a ventricle, wherein the net cover is formed by hollow tubes which are made by polyacrylate rubber and have a diameter of 1 mm. The rest is the same to the example 1.

Example 15

An active hydraulic ventricular attaching support system, comprises a net cover surrounding on a ventricle, wherein the net cover is formed by hollow tubes which are made by chlorosulfonated polyethylene gel and have a diameter of 1 mm. The rest is the same to the example 1.

Example 16

An active hydraulic ventricular attaching support system, comprises a net cover surrounding on a ventricle, wherein the net cover is formed by hollow tubes which are made by polyurethane gel and have a diameter of 1 mm. The rest is the same to the example 1.

Example 17

An active hydraulic ventricular attaching support system, comprises a net cover surrounding on a ventricle, wherein the net cover is formed by hollow tubes which are made by ethylene-propylene rubber and have a diameter of 1 mm. The rest is the same to the example 1.

Example 18

An active hydraulic ventricular attaching support system, comprises a net cover surrounding on a ventricle, wherein the net cover is formed by hollow tubes which are made by butyl rubber and have a diameter of 1 mm. The rest is the same to the example 1.

Example 19

An active hydraulic ventricular attaching support system, comprises a net cover surrounding on a ventricle, wherein the net cover is formed by hollow tubes which are made by barras and have a diameter of 1 mm. The rest is the same to the example 1.

Example 20

An active hydraulic ventricular attaching support system, comprises a net cover surrounding on a ventricle, wherein the net cover is formed by hollow tubes which are made by molecularly imprinted polymer which is capable of carrying specific medicine molecule. The hollow tubes have a diameter of 1 mm. The rest is the same to the example 1.

Example 21

An active hydraulic ventricular attaching support system, which has same basic structure to the example 1, comprises a net cover surrounding on a ventricle, wherein the net cover is formed by hollow tubes which are communicated completely. The net cover structure formed by the tubes structure is mounted on a surface of the heart as a whole. The hollow tubes are filled with normal saline. The net cover has two ends connected to an exterior of body and connected with a pressure producer. Therefore, the system are capable of not only supporting and restricting ventricular dilatation, but also actively applying a pressure not larger than 10 mmHg to the fluid inside the tubes. The pressure can be controlled in the range of 0-10 mmHg according to different heart failure condition. The hollow tubes are made by flexible silicone and have a diameter of 1.5 mm.

Example 22

An active hydraulic ventricular attaching support system, which has same basic structure to the example 21, is connected with an external hydraulic system of average pressure of 8 mmHg via the ends. The pressure is not larger than 10 mmHg, and changes periodically in sinusoid, which provides obvious ventricular power assistant effect to the patients of heart failure.

The following are examples of active hydraulic ventricular attaching support systems capable of administrating.

Example 23

An active hydraulic ventricular attaching support administration system, comprises a net cover surrounding on a ventricle, wherein the net cover is formed by hollow tubes which are made by flexible silicone and have a diameter of 1 mm. Apertures are provided on a side of the hollow tubes which attaches to the heart wall, and have a diameter of 0.5 mm. All the hollow tubes are communicated totally. The whole tubes system has two tubular ends having an inner diameter of 1.0 mm connected with an external pressure system or administration device. The external pressure system or administration device can be embodied as an ordinary injector of 5 ml or 50 ml, or embedded microscale administration pump or external microscale administration pump. By connecting the ends connected to the exterior of the active hydraulic ventricular attaching support administration system with the foregoing ordinary injector of 5 ml or 50 ml, or the embedded microscale administration pump or external microscale administration pump via the administration terminals or medical tubes, the external pressure system or administration device are connected with the system. The administration speed can be rapid injection of 5 ml or 50 ml liquid for once, or even and continuous injection of the external medicine fluid into the active hydraulic ventricular attaching support administration system in a speed of 0.01-1 ml/hour via the embedded microscale administration pump or external microscale administration pump.

Example 24

An active hydraulic ventricular attaching support administration system, comprises a net cover surrounding on a ventricle, wherein the net cover is formed by hollow tubes which are made by natural rubber and have a diameter of 1 mm. Apertures are provided on a side of the hollow tubes which attaches to the heart wall, and have a diameter of 0.4 mm. The rest is the same to the example 23.

Example 25

An active hydraulic ventricular attaching support administration system, comprises a net cover surrounding on a ventricle, wherein the net cover is formed by hollow tubes which are made by emulsion polymerized butadiene styrene rubber and have a diameter of 1 mm. Apertures are provided on a side of the hollow tubes which attaches to the heart wall, and have a diameter of 0.3 mm. The rest is the same to the example 23.

Example 26

An active hydraulic ventricular attaching support administration system, comprises a net cover surrounding on a ventricle, wherein the net cover is formed by hollow tubes which are made by solution polymerized butadiene styrene rubber and have a diameter of 1 mm. Apertures are provided on a side of the hollow tubes which attaches to the heart wall, and have a diameter of 0.4 mm. The rest is the same to the example 23.

Example 27

An active hydraulic ventricular attaching support administration system, comprises a net cover surrounding on a ventricle, wherein the net cover is formed by hollow tubes which are made by elastoplastics and have a diameter of 1 mm. Apertures are provided on a side of the hollow tubes which attaches to the heart wall, and have a diameter of 0.5 mm. All the hollow tubes are communicated completely. The rest is the same to the example 23.

Example 28

An active hydraulic ventricular attaching support administration system, comprises a net cover surrounding on a ventricle, wherein the net cover is formed by hollow tubes which are made by cis-1,4-polybutadiene rubber and have a diameter of 1 mm. Apertures are provided on a side of the hollow tubes which attaches to the heart wall, and have a diameter of 0.5 mm. The rest is the same to the example 23.

Example 29

An active hydraulic ventricular attaching support administration system, comprises a net cover surrounding on a ventricle, wherein the net cover is formed by hollow tubes which are made by polyisoprene rubber and have a diameter of 1 mm. Apertures are provided on a side of the hollow tubes which attaches to the heart wall, and have a diameter of 0.5 mm. The rest is the same to the example 23.

Example 30

An active hydraulic ventricular attaching support administration system, comprises a net cover surrounding on a ventricle, wherein the net cover is formed by hollow tubes which are made by neoprene and have a diameter of 1 mm. Apertures are provided on a side of the hollow tubes which attaches to the heart wall, and have a diameter of 0.5 mm. The rest is the same to the example 23.

Example 31

An active hydraulic ventricular attaching support administration system, comprises a net cover surrounding on a ventricle, wherein the net cover is formed by hollow tubes which are made by fluoric silica gel and have a diameter of 1 mm. Apertures are provided on a side of the hollow tubes which attaches to the heart wall, and have a diameter of 0.5 mm. The rest is the same to the example 23.

Example 32

An active hydraulic ventricular attaching support administration system, comprises a net cover surrounding on a ventricle, wherein the net cover is formed by hollow tubes which are made by hydrogenation butyronitrile gel and have a diameter of 1 mm. Apertures are provided on a side of the hollow tubes which attaches to the heart wall, and have a diameter of 0.5 mm. The rest is the same to the example 23.

Example 33

An active hydraulic ventricular attaching support administration system, comprises a net cover surrounding on a ventricle, wherein the net cover is formed by hollow tubes which are made by fluoric rubber and have a diameter of 1 mm. Apertures are provided on a side of the hollow tubes which attaches to the heart wall, and have a diameter of 0.5 mm. The rest is the same to the example 23.

Example 34

An active hydraulic ventricular attaching support administration system, comprises a net cover surrounding on a ventricle, wherein the net cover is formed by hollow tubes which are made by silicone rubber and have a diameter of 1 mm. Apertures are provided on a side of the hollow tubes which attaches to the heart wall, and have a diameter of 0.5 mm. The rest is the same to the example 23.

Example 35

An active hydraulic ventricular attaching support administration system, comprises a net cover surrounding on a ventricle, wherein the net cover is formed by hollow tubes which are made by chlorine ester rubber and have a diameter of 1 mm. Apertures are provided on a side of the hollow tubes which attaches to the heart wall, and have a diameter of 0.5 mm. The rest is the same to the example 23.

Example 36

An active hydraulic ventricular attaching support administration system, comprises a net cover surrounding on a ventricle, wherein the net cover is formed by hollow tubes which are made by polyacrylate rubber and have a diameter of 1 mm. Apertures are provided on a side of the hollow tubes which attaches to the heart wall, and have a diameter of 0.5 mm. The rest is the same to the example 23.

Example 37

An active hydraulic ventricular attaching support administration system, comprises a net cover surrounding on a ventricle, wherein the net cover is formed by hollow tubes which are made by chlorosulfonated polyethylene gel and have a diameter of 1 mm. Apertures are provided on a side of the hollow tubes which attaches to the heart wall, and have a diameter of 0.5 mm. The rest is the same to the example 23.

Example 38

An active hydraulic ventricular attaching support administration system, comprises a net cover surrounding on a ventricle, wherein the net cover is formed by hollow tubes which are made by polyurethane gel and have a diameter of 1 mm. Apertures are provided on a side of the hollow tubes which attaches to the heart wall, and have a diameter of 0.5 mm. The rest is the same to the example 23.

Example 39

An active hydraulic ventricular attaching support administration system, comprises a net cover surrounding on a ventricle, wherein the net cover is formed by hollow tubes which are made by ethylene-propylene rubber and have a diameter of 1 mm. Apertures are provided on a side of the hollow tubes which attaches to the heart wall, and have a diameter of 0.5 mm. The rest is the same to the example 23.

Example 40

An active hydraulic ventricular attaching support administration system, comprises a net cover surrounding on a ventricle, wherein the net cover is formed by hollow tubes which are made by butyl rubber and have a diameter of 1 mm. Apertures are provided on a side of the hollow tubes which attaches to the heart wall, and have a diameter of 0.5 mm. The rest is the same to the example 23.

Example 41

An active hydraulic ventricular attaching support administration system, comprises a net cover surrounding on a ventricle, wherein the net cover is formed by hollow tubes which are made by barras and have a diameter of 1 mm. Apertures are provided on a side of the hollow tubes which attaches to the heart wall, and have a diameter of 0.5 mm. The rest is the same to the example 23.

Example 42

An active hydraulic ventricular attaching support administration system, comprises a net cover surrounding on a ventricle, wherein the net cover is formed by hollow tubes which are made by molecularly imprinted polymer which is capable of carrying specific medicine molecule. The hollow tubes have a diameter of 1 mm. Apertures are provided on a side of the hollow tubes which attaches to the heart wall, and have a diameter of 0.5 mm. The rest is the same to the example 23.

Example 43

An active hydraulic ventricular attaching support administration system, comprises a net cover surrounding on a ventricle, wherein the net cover is formed by hollow tubes having apertures, the material and construction of the hollow tubes are the same to the example 23. The apertures are provided on the side of the hollow tubes which attaches to the heart wall, but not the side away from the heart wall. The hollow tubes are filled with 1% lidocaine solution. The system has two tubular ends having an inner diameter of 1.0 mm connected with an external pressure system or administration device. The external pressure system or administration device is an ordinary injector of 5 ml. By directly connecting the ends connected to the exterior of the active hydraulic ventricular attaching support administration system with the administration terminal of the foregoing ordinary injector of 5 ml, the external pressure system or administration device are connected with the system. The administration speed is rapid injection of 5 ml 1% lidocaine solution for once into the active hydraulic ventricular attaching support administration system. The lidocaine can apply on the tissue on the ventricular wall via the aperture structure, so as to produce treatment effect. With the foregoing device, medicine and operation, the present invention provides hydraulic heart wall support and restriction effect, and medicine treatment effect to rapid arrhythmia.

Example 44

An active hydraulic ventricular attaching support administration system, comprises a net cover surrounding on a ventricle, wherein the net cover is formed by hollow tubes having apertures, the material and construction of the hollow tubes are the same to the example 23. The hollow tubes are filled with 1% lidocaine solution. The system has two tubular ends having an inner diameter of 1.0 mm connected with an external pressure system or administration device. The external pressure system or administration device is an ordinary injector of 50 ml. By directly connecting the ends connected to the exterior of the active hydraulic ventricular attaching support administration system with the administration terminal of the foregoing ordinary injector of 5 ml, or via medical tubes, the external pressure system or administration device are connected with the system. The administration speed is rapid injection of 50 ml 1% lidocaine solution for once into the active hydraulic ventricular attaching support administration system. The lidocaine can apply on the tissue on the ventricular wall via the aperture structure, so as to produce treatment effect. With the foregoing device, medicine and operation, the present invention provides hydraulic heart wall support and restriction effect, and medicine treatment effect to rapid arrhythmia.

Example 45

An active hydraulic ventricular attaching support administration system, comprises a net cover surrounding on a ventricle, wherein the net cover is formed by hollow tubes having apertures, the material and construction of the hollow tubes are the same to the example 23. The hollow tubes are filled with 1% lidocaine solution. The system has two tubular ends having an inner diameter of 1.0 mm connected with an external pressure system or administration device. The external pressure system or administration device is an external microscale administration pump. By directly connecting the ends connected to the exterior of the active hydraulic ventricular attaching support administration system with the administration terminal of the foregoing external microscale administration pump, or via medical tubes, the external pressure system or administration device are connected with the system. The administration speed is even and continuous injection of 1% lidocaine solution into the active hydraulic ventricular attaching support administration system in a speed of 1 ml/hour via the external microscale administration pump. The lidocaine can apply on the tissue on the ventricular wall via the aperture structure, so as to produce treatment effect. With the foregoing device, medicine and operation, the present invention provides hydraulic heart wall support and restriction effect, and medicine treatment effect to rapid arrhythmia.

Example 46

An active hydraulic ventricular attaching support administration system, comprises a net cover surrounding on a ventricle, wherein the net cover is formed by hollow tubes having apertures, the material and construction of the hollow tubes are the same to the example 23. The hollow tubes are filled with 1% lidocaine solution. The system has two tubular ends having an inner diameter of 1.0 mm connected with an external pressure system or administration device. The external pressure system or administration device is an embedded microscale administration pump. By directly connecting the ends connected to the exterior of the active hydraulic ventricular attaching support administration system with the administration terminal of the foregoing embedded microscale administration pump, or via medical tubes, the external pressure system or administration device are connected with the system. The administration speed is even and continuous injection of 1% lidocaine solution into the active hydraulic ventricular attaching support administration system in a speed of 1 ml/hour via the embedded microscale administration pump. The lidocaine can apply on the tissue on the ventricular wall via the aperture structure, so as to produce treatment effect. With the foregoing device, medicine and operation, the present invention provides hydraulic heart wall support and restriction effect, and medicine treatment effect to rapid arrhythmia.

Example 47

An active hydraulic ventricular attaching support administration system, comprises a net cover surrounding on a ventricle, wherein the net cover is formed by hollow tubes having apertures. The hollow tubes are filled with 10% lidocaine solution, for providing hydraulic heart wall support and restriction effect, and medicine treatment effect to rapid arrhythmia. The basic structure thereof is the same to the example 23.

Example 48

An active hydraulic ventricular attaching support administration system, comprises a net cover surrounding on a ventricle, wherein the net cover is formed by hollow tubes having apertures. The hollow tubes are filled with 20% lidocaine solution, for providing hydraulic heart wall support and restriction effect, and medicine treatment effect to rapid arrhythmia. The basic structure thereof is the same to the example 23.

Example 49

An active hydraulic ventricular attaching support administration system, comprises a net cover surrounding on a ventricle, wherein the net cover is formed by hollow tubes having apertures. The hollow tubes are filled with 30% lidocaine solution, for providing hydraulic heart wall support and restriction effect, and medicine treatment effect to rapid arrhythmia. The basic structure thereof is the same to the example 23.

Example 50

An active hydraulic ventricular attaching support administration system, comprises a net cover surrounding on a ventricle, wherein the net cover is formed by hollow tubes having apertures. The hollow tubes are filled with 40% lidocaine solution, for providing hydraulic heart wall support and restriction effect, and medicine treatment effect to rapid arrhythmia. The basic structure thereof is the same to the example 23.

Example 51

An active hydraulic ventricular attaching support administration system, comprises a net cover surrounding on a ventricle, wherein the net cover is formed by hollow tubes having apertures. The hollow tubes are filled with 50% lidocaine solution, for providing hydraulic heart wall support and restriction effect, and medicine treatment effect to rapid arrhythmia. The basic structure thereof is the same to the example 23.

Example 52

An active hydraulic ventricular attaching support administration system, comprises a net cover surrounding on a ventricle, wherein the net cover is formed by hollow tubes having apertures. The hollow tubes are filled with injection solution of traditional Chinese medicine, radices salviae miltiorrhizae, for providing hydraulic heart wall support and restriction effect, and medicine treatment effect to myocardial ischemia, myocardial infarction, and heart failure. The basic structure thereof is the same to the example 23.

Example 53

An active hydraulic ventricular attaching support administration system, comprises a net cover surrounding on a ventricle, wherein the net cover is formed by hollow tubes having apertures. The hollow tubes are filled with injection solution of traditional Chinese medicine, shengmai, for providing hydraulic heart wall support and restriction effect, and medicine treatment effect to myocardial ischemia, myocardial infarction, and heart failure. The basic structure thereof is the same to the example 23.

Example 54

An active hydraulic ventricular attaching support administration system, comprises a net cover surrounding on a ventricle, wherein the net cover is formed by hollow tubes having apertures. The hollow tubes are filled with injection solution of traditional Chinese medicine, Shenmai, for providing hydraulic heart wall support and restriction effect, and medicine treatment effect to myocardial ischemia, myocardial infarction, and heart failure. The basic structure thereof is the same to the example 23.

Example 55

An active hydraulic ventricular attaching support administration system, comprises a net cover surrounding on a ventricle, wherein the net cover is formed by hollow tubes having apertures. The hollow tubes are filled with injection solution of breviscapine, for providing hydraulic heart wall support and restriction effect, and medicine treatment effect to myocardial ischemia, myocardial infarction, and heart failure. The basic structure thereof is the same to the example 23.

Example 56

An active hydraulic ventricular attaching support administration system, comprises a net cover surrounding on a ventricle, wherein the net cover is formed by hollow tubes having apertures. The hollow tubes are filled with injection solution of Sodium Tanshinon II Asilate, for providing hydraulic heart wall support and restriction effect, and medicine treatment effect to myocardial ischemia, myocardial infarction, and heart failure. The basic structure thereof is the same to the example 23.

Example 57

An active hydraulic ventricular attaching support administration system, comprises a net cover surrounding on a ventricle, wherein the net cover is formed by hollow tubes having apertures. The hollow tubes are filled with injection solution of ilexonin A, for providing hydraulic heart wall support and restriction effect, and medicine treatment effect to myocardial ischemia, myocardial infarction, and heart failure. The basic structure thereof is the same to the example 23.

Example 58

An active hydraulic ventricular attaching support administration system, comprises a net cover surrounding on a ventricle, wherein the net cover is formed by hollow tubes having apertures. The hollow tubes are filled with injection solution of 3,4-Dihydroxyacetophenone, for providing hydraulic heart wall support and restriction effect, and medicine treatment effect to myocardial ischemia, myocardial infarction, and heart failure. The basic structure thereof is the same to the example 23.

Example 59

An active hydraulic ventricular attaching support administration system, comprises a net cover surrounding on a ventricle, wherein the net cover is formed by hollow tubes having apertures. The hollow tubes are filled with injection solution of Lanatoside C, for providing hydraulic heart wall support and restriction effect, and medicine treatment effect to heart failure. The basic structure thereof is the same to the example 23.

Example 60

An active hydraulic ventricular attaching support administration system, comprises a net cover surrounding on a ventricle, wherein the net cover is formed by hollow tubes having apertures. The hollow tubes are filled with injection solution of digoxin, for providing hydraulic heart wall support and restriction effect, and medicine treatment effect to heart failure. The basic structure thereof is the same to the example 23.

Example 61

An active hydraulic ventricular attaching support administration system, comprises a net cover surrounding on a ventricle, wherein the net cover is formed by hollow tubes having apertures. The hollow tubes are filled with injection solution of Strophanral, for providing hydraulic heart wall support and restriction effect, and medicine treatment effect to heart failure. The basic structure thereof is the same to the example 23.

Example 62

An active hydraulic ventricular attaching support administration system, comprises a net cover surrounding on a ventricle, wherein the net cover is formed by hollow tubes having apertures. The hollow tubes are filled with injection solution of Propranolol Hydrochloride, for providing hydraulic heart wall support and restriction effect, and medicine treatment effect to arrhythmia. The basic structure thereof is the same to the example 23.

Example 63

An active hydraulic ventricular attaching support administration system, comprises a net cover surrounding on a ventricle, wherein the net cover is formed by hollow tubes having apertures. The hollow tubes are filled with injection solution of Bretylium Tosilate, for providing hydraulic heart wall support and restriction effect, and medicine treatment effect to arrhythmia. The basic structure thereof is the same to the example 23.

Example 64

An active hydraulic ventricular attaching support administration system, comprises a net cover surrounding on a ventricle, wherein the net cover is formed by hollow tubes having apertures. The hollow tubes are filled with injection solution of Verapamil Hydrochloride, for providing hydraulic heart wall support and restriction effect, and medicine treatment effect to arrhythmia. The basic structure thereof is the same to the example 23.

Example 65

An active hydraulic ventricular attaching support administration system, comprises a net cover surrounding on a ventricle, wherein the net cover is formed by hollow tubes having apertures. The hollow tubes are filled with injection solution of Propafenone Hydrochloride, for providing hydraulic heart wall support and restriction effect, and medicine treatment effect to arrhythmia. The basic structure thereof is the same to the example 23.

Example 66

An active hydraulic ventricular attaching support administration system, comprises a net cover surrounding on a ventricle, wherein the net cover is formed by hollow tubes having apertures. The hollow tubes are filled with injection solution of Procainamide Hydrochloride, for providing hydraulic heart wall support and restriction effect, and medicine treatment effect to arrhythmia. The basic structure thereof is the same to the example 23.

Example 67

An active hydraulic ventricular attaching support administration system, comprises a net cover surrounding on a ventricle, wherein the net cover is formed by hollow tubes having apertures. The hollow tubes are filled with injection solution of Amiodarone Hydrochloride, for providing hydraulic heart wall support and restriction effect, and medicine treatment effect to arrhythmia. The basic structure thereof is the same to the example 23.

Example 68

An active hydraulic ventricular attaching support administration system, comprises a net cover surrounding on a ventricle, wherein the net cover is formed by hollow tubes having apertures. The hollow tubes are filled with injection solution of Metoprolol Tartrate, for providing hydraulic heart wall support and restriction effect, and medicine treatment effect to arrhythmia. The basic structure thereof is the same to the example 23.

Example 69

An active hydraulic ventricular attaching support administration system, comprises a net cover surrounding on a ventricle, wherein the net cover is formed by hollow tubes having apertures. The hollow tubes are filled with injection solution of Diltiazem Hydrochloride, for providing hydraulic heart wall support and restriction effect, and medicine treatment effect to myocardial ischemia. The basic structure thereof is the same to the example 23.

Example 70

An active hydraulic ventricular attaching support administration system, comprises a net cover surrounding on a ventricle, wherein the net cover is formed by hollow tubes having apertures. The hollow tubes are filled with injection solution of Isosorbide Dinitrate, for providing hydraulic heart wall support and restriction effect, and medicine treatment effect to myocardial ischemia. The basic structure thereof is the same to the example 23.

Example 71

An active hydraulic ventricular attaching support administration system, comprises a net cover surrounding on a ventricle, wherein the net cover is formed by hollow tubes having apertures. The hollow tubes are filled with injection solution of Metaraminol Bitartrate, for providing hydraulic heart wall support and restriction effect, and medicine treatment effect to myocardial ischemia. The basic structure thereof is the same to the example 23.

Example 72

An active hydraulic ventricular attaching support administration system, comprises a net cover surrounding on a ventricle, wherein the net cover is formed by hollow tubes having apertures. The hollow tubes are filled with injection solution of Isoprenaline Hydrochloride, for providing hydraulic heart wall support and restriction effect, and medicine treatment effect of anti-shock. The basic structure thereof is the same to the example 23.

Example 73

An active hydraulic ventricular attaching support administration system, comprises a net cover surrounding on a ventricle, wherein the net cover is formed by hollow tubes having apertures. The hollow tubes are filled with injection solution of Dobutamine Hydrochloride, for providing hydraulic heart wall support and restriction effect, and medicine treatment effect of anti-shock. The basic structure thereof is the same to the example 23.

Example 74

An active hydraulic ventricular attaching support administration system, comprises a net cover surrounding on a ventricle, wherein the net cover is formed by hollow tubes having apertures. The hollow tubes are filled with injection solution of Dopamine Hydrochloride, for providing hydraulic heart wall support and restriction effect, and medicine treatment effect of anti-shock. The basic structure thereof is the same to the example 23.

Example 75

An active hydraulic ventricular attaching support administration system, comprises a net cover surrounding on a ventricle, wherein the net cover is formed by hollow tubes having apertures. The hollow tubes are filled with injection solution of Noradrenaline Bitartrate, for providing hydraulic heart wall support and restriction effect, and medicine treatment effect of anti-shock. The basic structure thereof is the same to the example 23.

Example 76

An active hydraulic ventricular attaching support administration system, comprises a net cover surrounding on a ventricle, wherein the net cover is formed by hollow tubes having apertures. The hollow tubes are filled with injection solution of Adrenaline Hydrochloride, for providing hydraulic heart wall support and restriction effect, and medicine treatment effect of anti-shock. The basic structure thereof is the same to the example 23.

Example 77

An active hydraulic ventricular attaching support administration system, comprises a net cover surrounding on a ventricle, wherein the net cover is formed by hollow tubes which are made by flexible silicone and have a diameter of 1 mm. apertures are provided on a side of the hollow tubes which attaches to the heart wall, and have a diameter of 0.5 mm. All the hollow tubes form two independent areas, wherein the hollow tubes in each independent area are communicated, and the two independent areas are isolated. Each independent area has two tubular ends having an inner diameter of 1.0 mm connected with an external pressure system or administration device. The external pressure system or administration device can be embodied as an ordinary injector of 5 ml or 50 ml, or embedded microscale administration pump or external microscale administration pump. By connecting the ends connected to the exterior of the active hydraulic ventricular attaching support administration system with the foregoing ordinary injector of 5 ml or 50 ml, or the embedded microscale administration pump or external microscale administration pump via the administration terminals or medical tubes, the external pressure system or administration device are connected with the system. The administration speed can be rapid injection of 5 ml or 50 ml liquid for once, or even and continuous injection of the external medicine fluid into the active hydraulic ventricular attaching support administration system in a speed of 0.01-1 ml/hour via the embedded microscale administration pump or external microscale administration pump. The liquid pressure and liquid species in different independent areas of the active hydraulic ventricular attaching support administration system can be totally different. The net cover formed by the two foregoing tube structures is mounted on the surface of the heart as a whole.

Example 78

An active hydraulic ventricular attaching support administration system, comprises a net cover surrounding on a ventricle, wherein the net cover is formed by hollow tubes which are made by flexible silicone and have a diameter of 1 mm. Apertures are provided on a side of the hollow tubes which attaches to the heart wall, and have a diameter of 0.4 mm. All the hollow tubes form four independent areas in 2*2 arrays, wherein the hollow tubes in each independent area are communicated, and the four independent areas are isolated. Each independent area has two tubular ends having an inner diameter of 1.0 mm connected with an external pressure system or administration device. The external pressure system or administration device can be embodied as an ordinary injector of 5 ml or 50 ml, or embedded microscale administration pump or external microscale administration pump. By connecting the ends connected to the exterior of the active hydraulic ventricular attaching support administration system with the foregoing ordinary injector of 5 ml or 50 ml, or the embedded microscale administration pump or external microscale administration pump via the administration terminals or medical tubes, the external pressure system or administration device are connected with the system. The rest is the same to the example 77.

Example 79

An active hydraulic ventricular attaching support administration system, comprises a net cover surrounding on a ventricle, wherein the net cover is formed by hollow tubes. All the hollow tubes form six independent areas in 2*3 arrays, wherein the hollow tubes in each independent area are communicated, and the six independent areas are isolated. Each independent area has two tubular ends having an inner diameter of 1.0 mm connected with an external pressure system or administration device. The liquid pressure and liquid species in different independent areas can be totally different. The net cover formed by the foregoing tube structures is mounted on the surface of the heart as a whole. The rest is the same to the example 77.

Example 80

An active hydraulic ventricular attaching support administration system, comprises a net cover surrounding on a ventricle, wherein the net cover is formed by hollow tubes. All the hollow tubes form eight independent areas in 2*4 arrays, wherein the hollow tubes in each independent area are communicated, and the eight independent areas are isolated. Each independent area has two tubular ends having an inner diameter of 1.0 mm connected with an external pressure system or administration device. The liquid pressure and liquid species in different independent areas can be totally different. The net cover formed by the foregoing tube structures is mounted on the surface of the heart as a whole. The rest is the same to the example 77.

Example 81

An active hydraulic ventricular attaching support administration system, comprises a net cover surrounding on a ventricle, wherein the net cover is formed by hollow tubes. All the hollow tubes form ten independent areas in 2*5 arrays, wherein the hollow tubes in each independent area are communicated, and the ten independent areas are isolated. Each independent area has two tubular ends having an inner diameter of 1.0 mm connected with an external pressure system or administration device. The liquid pressure and liquid species in different independent areas can be totally different. The net cover formed by the foregoing tube structures is mounted on the surface of the heart as a whole. The rest is the same to the example 77.

Example 82

An active hydraulic ventricular attaching support administration system, comprises a net cover surrounding on a ventricle, wherein the net cover is formed by hollow tubes. All the hollow tubes form twelve independent areas in 2*6 arrays, wherein the hollow tubes in each independent area are communicated, and the twelve independent areas are isolated. Each independent area has two tubular ends having an inner diameter of 1.0 mm connected with an external pressure system or administration device. The liquid pressure and liquid species in different independent areas can be totally different. The net cover formed by the foregoing tube structures is mounted on the surface of the heart as a whole. The rest is the same to the example 77.

Example 83

An active hydraulic ventricular attaching support administration system, comprises a net cover surrounding on a ventricle, wherein the net cover is formed by hollow tubes. All the hollow tubes form sixteen independent areas in 2*8 arrays, wherein the hollow tubes in each independent area are communicated, and the sixteen independent areas are isolated. Each independent area has two tubular ends having an inner diameter of 1.0 mm connected with an external pressure system or administration device. The liquid pressure and liquid species in different independent areas can be totally different. The net cover formed by the foregoing tube structures is mounted on the surface of the heart as a whole. The rest is the same to the example 77.

Example 84

An active hydraulic ventricular attaching support administration system, comprises a net cover surrounding on a ventricle, wherein the net cover is formed by hollow tubes. All the hollow tubes form twenty independent areas in 2*10 arrays, wherein the hollow tubes in each independent area are communicated, and the twenty independent areas are isolated. Each independent area has two tubular ends having an inner diameter of 1.0 mm connected with an external pressure system or administration device. The liquid pressure and liquid species in different independent areas can be totally different. The net cover formed by the foregoing tube structures is mounted on the surface of the heart as a whole. The rest is the same to the example 77. A method of transplanting the active hydraulic ventricular attaching support administration system comprises the steps of: cutting a hole or in minimally invasive into thorax to expose the heart, with or without in vitro circulation, suturing the active hydraulic ventricular attaching support administration system onto a surface of the ventricular wall.

Example 85

An active hydraulic ventricular attaching support administration system, which has same basic structure to the example 77, comprises a net cover surrounding on a ventricle, wherein the net cover is formed by hollow tubes which are communicated completely. The net cover structure formed by the tubes structure is mounted on a surface of the heart as a whole. The net cover has two ends connected to an exterior of body and connected with an external hydraulic system not larger than 8 mmHg. The hollow tubes are filled with lidocaine solution of any concentration. Therefore, the system are capable of restricting ventricular dilatation. The hollow tubes are made by flexible silicone and have a diameter of 2 mm. Apertures are provided on a side of the hollow tubes which attaches to the heart wall, and have a diameter of 1.0 mm, for permeating the medicine fluid rapidly and strongly controlling ventricular fibrillation. A method of transplanting the active hydraulic ventricular attaching support administration system comprises the steps of: cutting out thorax at middle of breastbone to expose the heart, with or without in vitro circulation, suturing the active hydraulic ventricular attaching support administration system onto a surface of the ventricular wall.

Example 86

An active hydraulic ventricular attaching support administration system, which has same basic structure to the example 77, is connected with an external hydraulic system of average pressure of 8 mmHg via the ends. The pressure is not larger than 10 mmHg, and changes periodically in sinusoid, which provides obvious ventricular power assistant effect to the patients of heart failure. A method of transplanting the active hydraulic ventricular attaching support administration system comprises the steps of: cutting out thorax at dorsal lateral to expose the heart, with or without in vitro circulation, suturing the active hydraulic ventricular attaching support administration system onto a surface of the ventricular wall.

Example 87

An active hydraulic ventricular attaching support administration system, which has same basic structure to the example 77, further comprises a flexible silicone membrane having a thickness of 0.01-1.0 mm, and a permeability of 0-10 mol/m$^2$·min for the fluid. Due to the existing of the membrane, the medicine fluid inside the active hydraulic ventricular attaching support administration system will not enter the thorax rapidly, and thus maintains a certain high and controllable pressure inside the tubes. Therefore, after injecting various kinds of medicines, the system will not only rapidly and obviously reduce the seizure frequency and seizure degree of diseases such as rapid arrhythmia and myocardial ischemia, but also maintain a quite high active supporting and restricting effect to the ventricular wall. A method of transplanting the active hydraulic ventricular attaching support administration system comprises the steps of: under a thoracoscope, cutting a hole or in minimally invasive into thorax to expose the heart, with or without in vitro circulation, adhering the active hydraulic ventricular attaching support administration system onto a surface of the ventricular wall with a self-adhesive biologic adhesive.

Example 87

The basic structure is the same to the example 77. The tubes are filled with bone marrow stem cells nutrient solution. A PVPF polycarbonate membrane having a hole diameter of 3-8 μm, or a PVPF polycarbonate membrane having a hole diameter of 5-8 μm covered by glutin or cellulose, is attached outside the apertures of the system. The membrane has a thickness of 0.01-1.0 mm, and a permeability of 0-10$^8$ stem cells/hour. The system is capable of obviously increasing the myocardial regeneration after myocardial infarction, and effectively inhibiting the myocardial remodeling, so as to reduce the incidence rate and the death rate after heart failure.

What is claimed is:

1. An active hydraulic ventricular attaching support system, comprising:
   a net cover for surrounding a ventricle, wherein the net cover is formed by hollow tubes, wherein all the hollow tubes are communicated with each other to form several independent areas, wherein the hollow tubes are communicated with each other within the areas while the areas are not communicated with each other,
   wherein the net cover is adapted to be mounted on a heart of a human being or an animal as an entirety, the hollow tubes are filled with various fluids of different physical characteristics, the fluids producing corresponding reactive pressure with respect to actions of the heart, effecting on the ventricle, the pressure produced by passive expansion of the net cover that is applied on the heart through constriction of the heart;
   wherein a plurality of apertures are provided on a surface of the hollow tubes forming the net cover for administering a fluid, wherein the surface attaches to the ventricular wall in such a manner that a medicine compound or an embryonic stem cell or a bone marrow stem cell in the fluid inside the hollow tubes is capable of effecting on cardiac muscle directly, and producing a direct pharmacological action under a high local concentration applied to the cardiac muscle or other heart tissues without entering blood circulation;
   wherein one or more membranes are attached outside the apertures; and
   wherein the membrane has permeability that selectively allows medicine molecules of a certain size, weight, electric quantity, or molecular configuration to pass so as to further control the species, dose and speed of administration.

2. The active hydraulic ventricular attaching support system as recited in claim 1, wherein a diameter of the apertures is less than a half of the diameter of the hollow tubes.

3. The active hydraulic ventricular attaching support system as recited in claim 2, wherein the diameter of the hollow tubes is 1-2 mm and wherein the diameter of the apertures is 0.5-1.0 mm.

4. The active hydraulic ventricular attaching support system as recited in claim 1, wherein the net cover with the apertures is connected to an administrating system adapted to be placed outside the body of the human being or the animal via the ends adapted to be connected with the exterior of body, in such a manner that medicine from outside is capable of spreading throughout the net cover or concentrate in an independent area of the net cover via the hollow tubes, and then be applied to the ventricle via the apertures in such a manner that the species, dose, and concentration of medicine, and the time and period of administration as well, the whole administration profile can be adjusted at any time, so as to control the treatment to increase the treatment effect.

5. The active hydraulic ventricular attaching support system as recited in claim 1, wherein the hollow tubes are made of flexible silicone, natural rubber, emulsion polymerized butadiene styrene rubber, solution polymerized butadiene styrene rubber, elastoplastics, cis-1,4-polybutadiene rubber, polyisoprene rubber, neoprene, fluoric silica gel, hydrogenation butyronitrile gel, fluoric rubber, silicone rubber, chlorine ester rubber, chlorosulfonated polyethylene gel, polyurethane gel, ethylene-propylene rubber, butyl rubber or barras so as to make sure that the tubes that are filled with the fluids have good capacity and flexibility, and so as to ensure good hydraulic reactivity for the expected hydraulic ventricle support effect.

6. The active hydraulic ventricular attaching support system as recited in claim 1, wherein the hollow tubes are made of molecularly imprinted polymer which is capable of carrying a specific medicine molecule.

7. The active hydraulic ventricular attaching support system as recited in claim 1, wherein the hollow tubes are filled with normal saline,
   wherein the net cover has two ends adapted to be connected to an exterior of a body of the human being or an animal and connected with a pressure producer in such a manner that the system is capable of not only supporting and restricting ventricular dilatation, but also actively applying a pressure not larger than 10 mmHg to the fluid inside the tubes, and wherein the pressure is controlled in the range of 0-10 mmHg according to different heart failure condition.

8. The active hydraulic ventricular attaching support system as recited in claim 1, wherein the system is connected with an external hydraulic system with an average pressure of 8 mmHg via the ends, wherein the pressure is not larger than 10 mmHg, and changes periodically and sinusoidally providing ventricular power assistant effect to the patients of heart failure; and wherein the hollow tubes form several independent areas, wherein liquid pressure and liquid species in different independent areas are totally different.

9. The active hydraulic ventricular attaching support administration system as recited in claim 1, wherein the net cover has two or more ends adapted to be connected to an exterior of a body of the human being or the animal, and wherein the hollow tubes form the several independent areas, each of the independent areas forming the net cover having two or more ends connected to the exterior of the body of the human being or the animal, wherein the ends adapted to be connected to the exterior of body are connected using instruments or equipment outside the body using a good sealing and firm connection, so as to avoid any gap or hole, any leaking of gas or fluid inside the tubes, or entering of external fluid, gas, solid or microorganism into the tubes, for realizing basic hydraulic function, each independent area has at least two ends adapted to be connected with the exterior of body of the human being or the animal and forming a through way in such a manner that a pressure determined outside the body of the human being or the animal is transferred to the ventricle via the fluid inside the tubes, and applies stronger and adjustable restriction effect.

10. The active hydraulic ventricular attaching support system as recited in claim 9, wherein the ends of the net cover are connected to a force pump system in vitro, so as to adjust pressure of the fluid.

11. An active hydraulic ventricular attaching support system, comprising:

a net cover for surrounding a ventricle, wherein the net cover is formed by hollow tubes, wherein all the hollow tubes are communicated with each other to form several independent areas, wherein the hollow tubes are communicated with each other within the areas while the areas are not communicated with each other, wherein the net cover is adapted to be mounted on a heart of a human being or an animal as an entirety, the hollow tubes are filled with various fluids of different physical characteristics, the fluids producing corresponding reactive pressure with respect to actions of the heart, effecting on the ventricle, the pressure produced by passive expansion of the net cover that is applied on the heart through constriction of the heart;

wherein a plurality of apertures are provided on a surface of the hollow tubes forming the net cover for administering a fluid, wherein the surface attaches to the ventricular wall in such a manner that a medicine compound or an embryonic stem cell or a bone marrow stem cell in the fluid inside the hollow tubes is capable of effecting on cardiac muscle directly, and producing a direct pharmacological action under a high local concentration applied to the cardiac muscle or other heart tissues without entering blood circulation;

wherein the net cover has two or more ends adapted to be connected to an exterior of a body of the human being or the animal, in such a manner that a pressure determined outside the body is transferred to the ventricle via the fluid inside the tubes;

wherein the ends of the net cover are connected to a force pump system or an administrating system in vitro, in such a manner that medicine delivered from outside is capable of filling and spreading throughout the net cover, and then applied to the ventricle via the apertures in such a manner that the species, concentration, dose of medicine, and speed of administration is capable of being adjusted outside the body of the human being or the animal;

wherein one or more membranes are attached outside the apertures;

wherein the membrane has a permeability that selectively allows medicine molecules of certain size, weight, electric quantity, or molecular configuration to pass, so as to further control the species, dose and speed of administration, wherein the hollow tubes are made of a flexible material selected from the group consisting of rubber, silica gel, silicone, and other materials of macromolecules and flexible physical character so as to make sure that the tubes filled with the fluids have good capacity and flexibility to ensure good hydraulic reactivity for the expected hydraulic ventricle support effect.

12. An active hydraulic ventricular attaching support system, comprising:

a net cover for surrounding a ventricle, wherein the net cover is formed by hollow tubes, wherein all the hollow tubes are communicated with each other to form several independent areas, wherein the hollow tubes are communicated with each other within the areas while the areas are not communicated with each other, wherein the net cover is adapted to be mounted on a heart of a human being or an animal as an entirety, the hollow tubes are filled with various fluids of different physical characteristics, the fluids producing corresponding reactive pressure with respect to actions of the heart, effecting on the ventricle, the pressure produced by passive expansion of the net cover that is applied on the heart through constriction of the heart;

wherein a plurality of apertures are provided on a surface of the hollow tubes forming the net cover for administering a fluid, wherein the surface attaches to the ventricular wall in such a manner that a medicine compound or an embryonic stem cell or a bone marrow stem cell in the fluid inside the hollow tubes is capable of effecting on cardiac muscle directly, and producing a direct pharmacological action under a high local concentration applied to the cardiac muscle or other heart tissues without entering blood circulation;

wherein the apertures are provided on the side of the hollow tubes that attaches to the heart wall, but not the side away from the heart wall, wherein the hollow tubes are filled with 1% lidocaine solution, wherein the system has two tubular ends having an inner diameter of 1.0 mm connected with an external pressure system or administration device; the external pressure system or administration device being an ordinary injector of 5 ml; wherein the ends are directly connected to the exterior of the active hydraulic ventricular attaching support administration system with the administration terminal of the ordinary injector of 5 ml, the administration speed is rapid injection of 5 ml 1% lidocaine solution for once into the active hydraulic ventricular attaching support administration system, wherein the lidocaine is applied on the tissue on the ventricular wall via the aperture structure so as to produce a treatment effect so as to provide hydraulic heart wall support and restriction effect, and medicine treatment effect to rapid arrhythmia.

13. The active hydraulic ventricular attaching support administration system as recited in claim 12, further comprising a flexible silicone membrane having a thickness of 0.01-1.0 mm, and a permeability of 0-10 mol/m²·min for the fluid;
wherein the membrane prevents the medicine fluid inside the active hydraulic ventricular attaching support administration system from entering the thorax rapidly, and thus maintains a high and controllable pressure inside the tubes in such a manner that after injecting the various kinds of medicine, the system will not only rapidly reduce the seizure frequency and seizure degree of diseases such as rapid arrhythmia and myocardial ischemia, but also maintain a high active supporting and restricting effect to the ventricular wall.

14. The active hydraulic ventricular attaching support administration system as recited in claim 12 wherein the tubes are filled with bone marrow stem cells nutrient solution;
wherein a PVPF polycarbonate membrane having a hole diameter of 3-8 μm, or a PVPF polycarbonate membrane having a hole diameter of 5-8 μm covered by glutin or cellulose, is attached to the things outside the apertures of the system;
wherein the membrane has a thickness of 0.01-1.0 mm, and a permeability of 0-$10^8$ stem cells/hour; and
wherein the system is capable of increasing myocardial regeneration after myocardial infarction, and effectively inhibiting myocardial remodeling, so as to reduce the incidence rate and the death rate after heart failure.

* * * * *